US008965505B2

(12) United States Patent
Charlton et al.

(10) Patent No.: US 8,965,505 B2
(45) Date of Patent: *Feb. 24, 2015

(54) UTILIZATION OF MORPHOLOGY DISCRIMINATION AFTER UNDERSENSING DETERMINATION FOR UNDERLYING RHYTHMS IN THE THERAPY ZONE

(71) Applicant: Medtronic, Inc., Minneapolis, MN (US)

(72) Inventors: Sandra B. Charlton, Little Rock, AR (US); Troy E. Jackson, New Brighton, MN (US); Benjamin P. Rhodes, Columbia Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/832,202

(22) Filed: Mar. 15, 2013

(65) Prior Publication Data

US 2014/0277222 A1    Sep. 18, 2014

(51) Int. Cl.
*A61N 1/365* (2006.01)
*A61N 1/39* (2006.01)
*A61N 1/362* (2006.01)

(52) U.S. Cl.
CPC ............ *A61N 1/3931* (2013.01); *A61N 1/3622* (2013.01); *A61N 1/3962* (2013.01)
USPC ......................... 607/14; 607/4; 607/5; 607/27

(58) Field of Classification Search
CPC ... A61N 1/362; A61N 1/3621; A61N 1/3622; A61N 1/3624; A61N 1/365; A61N 1/368
USPC .......... 607/2–5, 9, 14, 25; 600/508, 509, 518, 600/521
See application file for complete search history.

(56) References Cited

U.S. PATENT DOCUMENTS

| 5,545,186 | A  | 8/1996  | Olson    |
|-----------|----|---------|----------|
| 5,755,736 | A  | 5/1998  | Gillberg |
| 6,129,745 | A  | 10/2000 | Sun      |
| 6,393,316 | B1 | 5/2002  | Gillberg |
| 6,567,691 | B1 | 5/2003  | Stadler  |
| 7,031,771 | B2 | 4/2006  | Brown    |

(Continued)

FOREIGN PATENT DOCUMENTS

WO    WO 2011/136950 A1    11/2011

OTHER PUBLICATIONS (PCT/US2014/020585) PCT Notification of Transmittal of the International Search Report and the Written Opinion of the International Searching Authority.

*Primary Examiner* — Allen Porter, Jr.
(74) *Attorney, Agent, or Firm* — Michael C. Soldner

(57) ABSTRACT

A medical device and method for detecting and classifying cardiac rhythm episodes that includes a sensing module to sense cardiac events, a therapy delivery module, and a detection module configured to determine intervals between the sensed cardiac events, determine a predetermined cardiac episode is occurring in response to the determined intervals, determine whether a ventricular rate is greater than an atrial rate in response to the determined intervals, determine whether undersensing is occurring in response to the ventricular rate being greater than the atrial rate, perform a supraventricular tachycardia (SVT) discrimination analysis in response to undersensing occurring, and control the therapy delivery module to deliver therapy in response to the SVT discrimination analysis.

12 Claims, 4 Drawing Sheets

(56) References Cited

U.S. PATENT DOCUMENTS

| | | |
|---|---|---|
| 7,062,322 B2 | 6/2006 | Stadler |
| 7,242,978 B2 | 7/2007 | Cao |
| 7,783,354 B2 | 8/2010 | Gunderson |
| 7,831,304 B2 | 11/2010 | Cao |
| 8,073,536 B2 | 12/2011 | Gunderson |
| 8,121,682 B2 | 2/2012 | Whitman |
| 8,137,269 B2 | 3/2012 | Sheikhzadeh-Nadjar |
| 2010/0331903 A1 | 12/2010 | Zhang |
| 2011/0112417 A1 | 5/2011 | Gunderson |
| 2011/0270107 A1 | 11/2011 | Zhang |
| 2011/0282405 A1* | 11/2011 | Hauck et al. ............ 607/5 |
| 2012/0016432 A1 | 1/2012 | Westendorp et al. |

* cited by examiner

UTILIZATION OF MORPHOLOGY DISCRIMINATION AFTER UNDERSENSING DETERMINATION FOR UNDERLYING RHYTHMS IN THE THERAPY ZONE

CROSS-REFERENCE TO RELATED APPLICATION

Cross-reference is hereby made to the commonly-assigned related U.S. Application No. 13/832,162, entitled "UTILIZATION OF MORPHOLOGY DISCRIMINATION AFTER UNDERSENSING FOR UNDERLYING RHYTHMS IN THE THERAPY ZONE," to Charlton et al., filed concurrently herewith and incorporated herein by reference in it's entirety.

FIELD OF THE DISCLOSURE

The disclosure relates generally to medical devices and, in particular, to an apparatus and method for detecting and discriminating cardiac tachyarrhythmias.

BACKGROUND

Implantable medical devices (IMDs), including pacemakers and implantable cardioverter-defibrillators (ICDs), record cardiac electrogram (EGM) signals for detecting the heart rhythm and responding as needed with pacing therapy or high-voltage cardioversion/defibrillation therapy. Numerous criteria may be applied to the EGM signals for detecting arrhythmias and for discriminating between different types of arrhythmias, such as supraventricular tachycardia (SVT), ventricular tachycardia (VT) and ventricular fibrillation (VF). Forms of SVT, including sinus tachycardia, atrial fibrillation and atrial flutter, can be referred to as "non-treatable" or "non-shockable" rhythms in that typically a cardioversion/defibrillation shock delivered to the heart is undesirable for treating these more benign rhythms. Sustained VT and VF, on the other hand, can be referred to as "treatable" or "shockable" rhythms because such sustained rhythms are more serious and potentially life-threatening. Detection of a sustained VT or VF is generally treated by anti-tachycardia pacing (ATP) or a cardioversion/defibrillation shock. One important goal of a tachyarrhythmia detection algorithm is to detect all treatable VT and VF episodes.

Another goal is to avoid delivering a shock therapy when a fast rhythm is a non-treatable rhythm. SVT is sometimes inappropriately detected as VT or VF when the SVT rate falls in a VT or VF rate zone (i.e. therapy zone). The inappropriate VT or VF detection can result in the patient receiving an unnecessary cardioversion/defibrillation shock. Therefore, what is needed is a system and method that provides reliable detection and discrimination of tachyarrhythmias and reduces the likelihood of inappropriate VT or VF detections in the presence of SVT.

DETAILED DESCRIPTION

In the following description, references are made to illustrative embodiments. It is understood that other embodiments may be utilized without departing from the scope of the disclosure.

In ICD detection algorithms, oversensing of T-waves or non-cardiac noise can result in the detection of a ventricular rate in a therapy zone. Detection of oversensing may be implemented to reduce the likelihood of making a false positive VT or VF detection. T-wave oversensing (TWOS) analysis is typically performed to prevent confirmation of a VT or VF detection when TWOS is present and the underlying true ventricular rate is not in a therapy zone. If a true underlying rate is in a therapy zone, even after accounting for TWOS, the VT or VF is confirmed and therapy is delivered. The true underlying rate, however, may be a supraventricular rhythm being conducted to the ventricles. While TWOS analysis may reduce the likelihood of a false positive VT or VF detection when no SVT is present, it does not, in and of itself, enable a correct classification of the episode as an SVT when the fast ventricular rate is being conducted from the ventricles.

Typically, a discrimination technique for classifying a tachyarrhythmia as an SVT is performed when the ventricular rate is not faster than the atrial rate and less than an SVT limit. If the sensed ventricular rate is faster than the atrial rate due to TWOS, a supraventricular rhythm will go undetected because SVT discrimination techniques will not be enabled due to the sensed ventricular rate being greater than the atrial rate.

As such, when TWOS is present and causing a sensed ventricular rate to be greater than an atrial rate, a positive detection of SVT may never be made since SVT discrimination techniques will not be employed. A false positive VT or VF detection may still be made under these circumstances if the true underlying ventricular rate is in the therapy zone. The apparatus and techniques described herein address this situation by providing a detection method that enables a positive SVT detection to be made when ventricular oversensing or atrial undersensing causes a sensed ventricular rate to be faster than a sensed atrial rate in a dual chamber ICD system. By providing an ICD system that enables true positive detections of SVT in the presence of TWOS or atrial undersensing, the specificity of the overall detection algorithm is improved and the occurrence of unnecessary shock therapy may be reduced.

Figure 1:
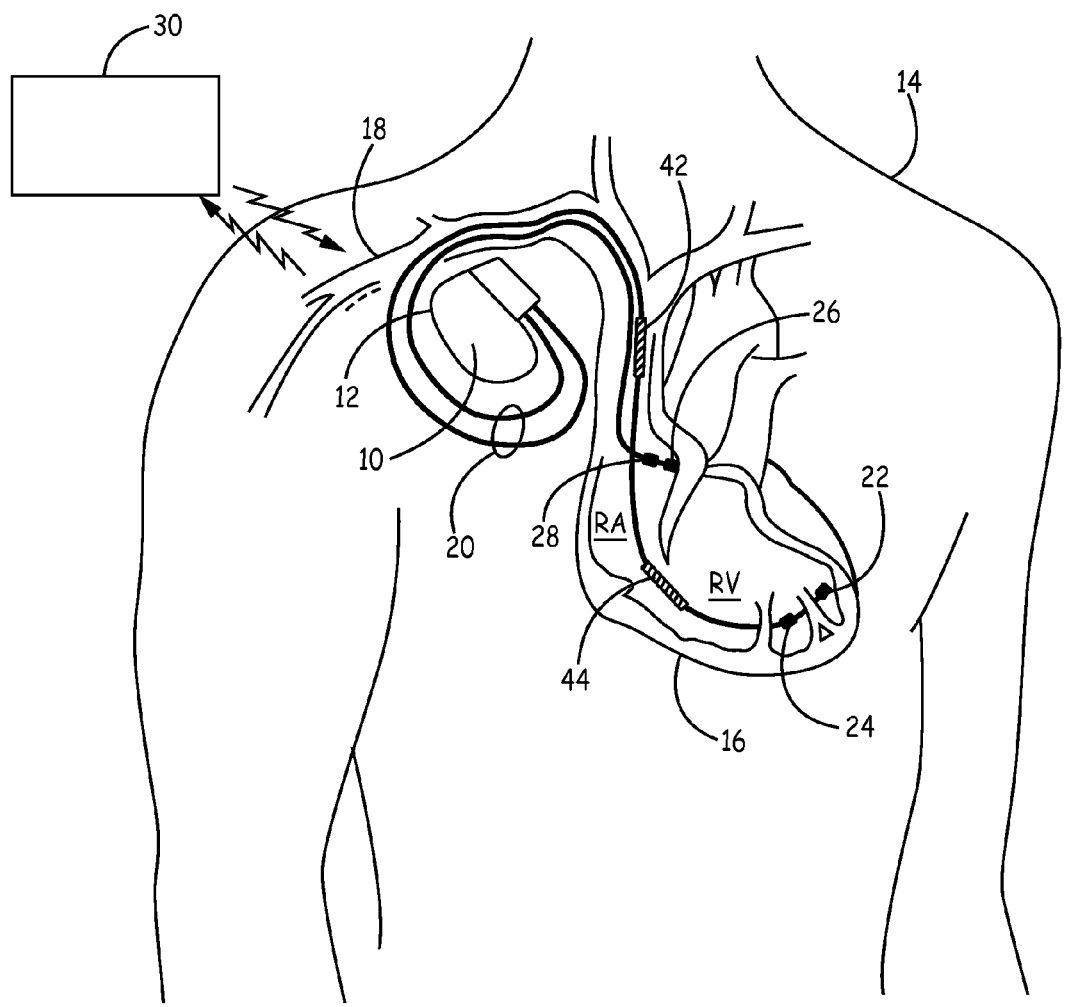
FIG. 1 is a schematic diagram of an implantable medical device system according to one embodiment.

FIG. 1 is a schematic diagram of an implantable medical device system 8 according to one embodiment. As illustrated in FIG. 1, a system 8 for sensing cardiac events (e.g. P-waves and R-waves) and detecting and discriminating tachyarrhythmia episodes includes IMD 10, embodied as an ICD capable of delivering pacing, cardioversion and defibrillation therapy to the heart 16 of a patient 14. One or more leads, collectively identified with reference numeral 20 in FIG. 1, are electrically coupled to the IMD 10 and extend into the patient's heart 16 via a vein 18. Leads 20 include electrodes 22 and 24 shown positioned in the patient's right ventricle (RV) and electrodes 26 and 28 positioned in the patient's right atrium (RA) for sensing EGM signals and pacing in the RV and RA, respectively. Leads 20 additionally carry high voltage coil electrodes 42 and 44 used to deliver cardioversion and defibrillation shock pulses. The leads 20 are used to acquire intracardiac EGM signals from the patient 14 and to deliver therapy in response to the acquired data. IMD 10 is shown as a dual chamber ICD, but in some embodiments, system 8 may be embodied as a multi-chamber system including a coronary sinus lead extending into the right atrium, through the coronary sinus and into a cardiac vein to position electrodes along the left ventricle (LV) for sensing LV EGM signals and pacing the LV.

IMD circuitry and associated battery(ies) are housed within a sealed housing 12, which may itself be conductive so as to serve as an electrode for use as an indifferent electrode during pacing or sensing or as an active electrode during defibrillation. As such, housing 12 is also referred to herein as "housing electrode" 12.

The EGM signal data acquired by IMD 10 can be transmitted to an external device 30, which may be embodied as a programmer, e.g. used in a clinic or hospital to communicate with IMD 10 via wireless telemetry. External device 30 may alternatively be embodied as a computer, home monitor, or hand-held device including cell phones, smart phones or the like, enabled to communicate directly or indirectly with IMD 10 for retrieving EGM signal data acquired by IMD 10. External device 30 may be coupled to a remote patient monitoring system, such as Carelink®, available from Medtronic, Inc., Minneapolis, Minn. Device 30 is used to program commands or operating parameters into IMD 10 for controlling IMD function and to interrogate IMD 10 to retrieve data, including device operational data as well as physiological data retrieved in real-time or accumulated in IMD memory.

Figure 2:
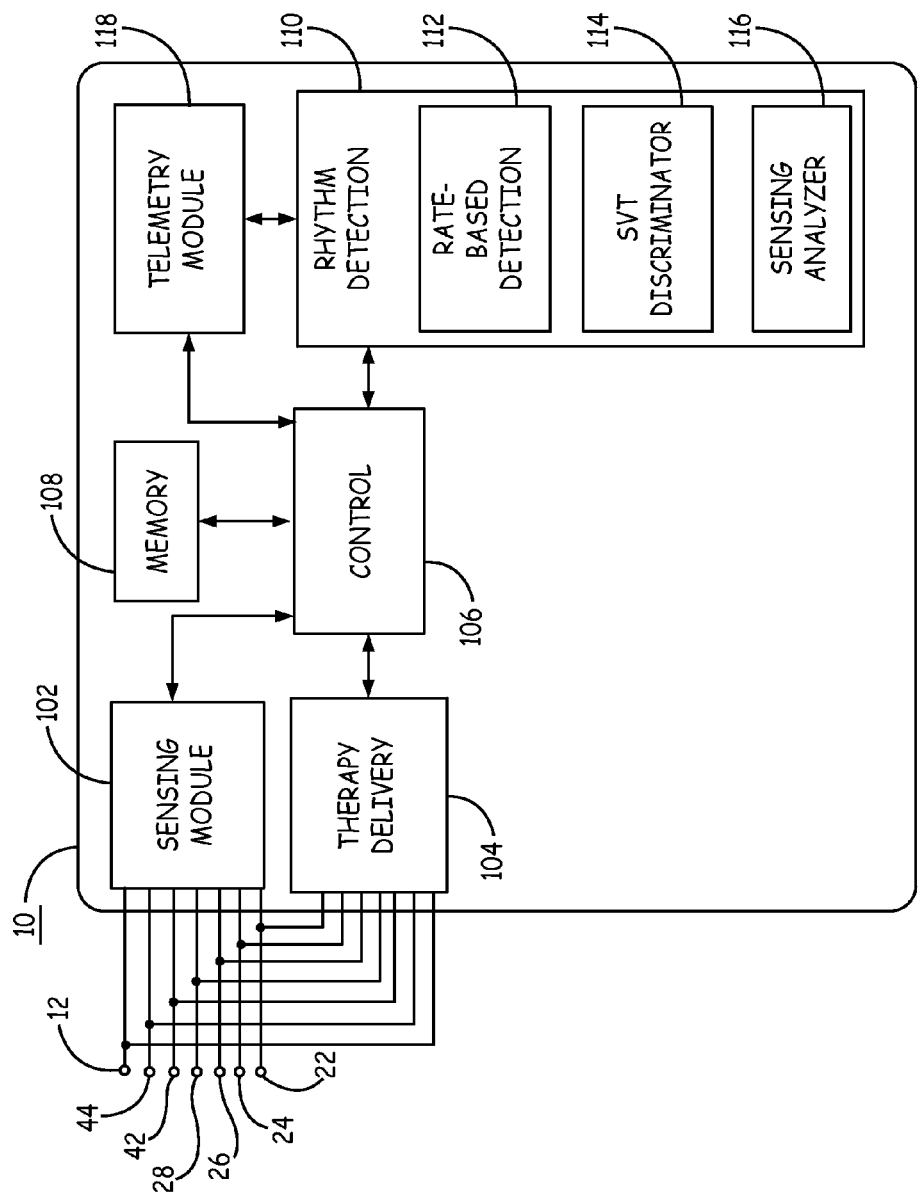
FIG. 2 is a functional block diagram of the system shown in FIG. 1 according to one embodiment.

FIG. 2 is a functional block diagram of IMD 10 according to one embodiment. IMD 10 includes a sensing module 102, a therapy delivery module 104, a control unit 106 and associated memory 108, a rhythm detection module 110, and telemetry module 118. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Sensing module 102 receives cardiac electrical signals from electrodes carried by leads 20 for sensing cardiac events attendant to the depolarization of myocardial tissue, e.g. P-waves and R-waves. Sensing module 102 may include a switch module for selectively coupling electrodes 22, 24, 26, 28, 42, 44, and housing electrode 12 to sensing module 102 in order to monitor electrical activity of heart 16. The switch module may include a switch array, switch matrix, multiplexer, or any other type of switching device suitable to selectively couple electrodes to sensing module 102. In some examples, control unit 106 selects the electrodes to function as sense electrodes, or the sensing vector, via the switch module within sensing module 102.

Sensing module 102 may include multiple sensing channels, each of which may be selectively coupled to respective combinations of electrodes 22, 24, 26, 28, 42, 44 and housing 12 to detect electrical activity of a particular chamber of heart 16, e.g. an atrial sensing channel and a ventricular sensing channel. Each sensing channel may comprise an amplifier that outputs an indication to control unit 106 in response to sensing of a cardiac depolarization, in the respective chamber of heart 16. In this manner, control unit 106 and rhythm detection module 110 may receive sense event signals corresponding to the occurrence of sensed R-waves and P-waves in the respective chambers of heart 16. Sensing module 102 may further include digital signal processing circuitry for providing control unit 106 and/or rhythm detection module 110 with digitized EGM signals, which may be used for SVT discrimination by SVT discriminator 114 and for sensing analysis to detect possible undersensing and/or oversensing of cardiac events by sensing analyzer 116.

Memory 108 may include computer-readable instructions that, when executed by control unit 106 and rhythm detection module 110, cause IMD 10 to perform various functions attributed throughout this disclosure to IMD 10. The computer-readable instructions may be encoded within memory 108. Memory 108 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Control unit 106 may include any one or more of a microprocessor, a controller, a digital signal processor (DSP), an application specific integrated circuit (ASIC), a field-programmable gate array (FPGA), or equivalent discrete or integrated logic circuitry or state machine. In some examples, control unit 106 may include multiple components, such as any combination of one or more microprocessors, one or more controllers, one or more DSPs, one or more ASICs, or one or more FPGAs, as well as other discrete or integrated logic circuitry or state machines. The functions attributed to control unit 106 herein may be embodied as software, firmware, hardware or any combination thereof. Rhythm detection module 110 may be implemented as a portion of control unit 106. In one example, rhythm detection module 110 may, at least in part, be stored or encoded as instructions in memory 108 that are executed by control unit 106.

Control unit 106 includes a therapy control unit that controls therapy delivery module 104 to deliver electrical stimulation therapy, e.g., cardiac pacing, anti-tachyarrhythmia therapy, or shock pulses, to heart 16 according to a selected one or more therapy programs, which may be stored in memory 108. Therapy delivery module 104 is electrically coupled to electrodes 22, 24, 26, 28, 42, 44 and housing electrode 12 (all of which are shown in FIG. 1). Therapy delivery module 104 is configured to generate and deliver electrical stimulation therapy to heart 16 via selected combinations of electrodes 22, 24, 26, 28, 42, 44, and housing electrode 12.

Memory 108 stores intervals, counters, or other data used by processor 106 to control the delivery of pacing pulses by therapy delivery module 104. Such data may include intervals and counters used by processor 106 to control the delivery of pacing pulses to heart 16. The intervals and/or counters are, in some examples, used by processor 106 to control the timing of delivery of pacing pulses relative to an intrinsic or paced event in another chamber. Memory 108 also stores intervals for controlling cardiac sensing functions such as blanking intervals and refractory sensing intervals. Events sensed by the sense amplifiers are identified in part based on their occurrence outside a blanking interval and inside or outside of a refractory sensing interval.

Rhythm detection module 110 receives analog and/or digitized EGM signals and sensed event signals corresponding to R-waves and P-waves from sensing module 102 for use in cardiac rhythm episode detection and classification. In the embodiment shown, an interval- or rate-based detection module 112 applies various criteria or rules to the sensed event intervals for detecting a tachyarrhythmia episode. A prioritized rule based method for detecting tachyarrhythmias referred to as PR logic is implemented in commercially available Protecta™ DR or CRT-D devices from Medtronic, Inc., Minneapolis, Minn., and is one example of an interval-based detection method that may be implemented in rhythm detection module 110. Examples of detection techniques employing prioritized interval-based detection rules are generally described in commonly-assigned U.S. Pat. No. 5,545,186 (Olson, et al.), U.S. Pat. No. 5,755,736 (Gillberg et al.), U.S. Pat. No. 6,567,691 (Stadler), and U.S. Pat. No. 7,031,771

(Brown, et al.), all of which patents are hereby incorporated herein by reference in their entirety. However other interval- or rate-based detection methods may be utilized for detecting a cardiac rhythm falling in a VT or VF detection zone that do not necessarily rely on a prioritized rule-based algorithm.

Interval-based detection criteria performed by rate-based detection module 112 generally includes a definition of a tachycardia detection interval (TDI) and a fibrillation detection interval (FDI). RR intervals that are shorter than the TDI are counted by a VT counter and RR intervals that are shorter than the FDI are counted by a VF counter. In some embodiments, a combined counter counts intervals meeting either the TDI or FDI limit. When a counter reaches required number of intervals to detect (NID), which may be a required number of consecutive intervals or a required number out of a given number of consecutive intervals, for example 8 out of 12 intervals, a corresponding VT or VF detection is made. Rate-based detection module 112 may include additional prioritized rules that examine event or interval patterns or other criteria for making VT or VF episode detections using the event rate or intervals as a primary detection criterion.

As will be further described herein, in response to a rate-based or interval-based detection of a heart rhythm in a VT or VF detection zone, modules 114 and 116 may perform additional analysis to improve the specificity of the episode detection. SVT discriminator 114 is employed to discriminate between SVT and VT or VF when a ventricular rate is less than an SVT maximum limit. For example, if interval-based VT detection criteria are met, but the ventricular rate is less than an SVT limit and the ventricular rate and the atrial rate are approximately equal or in 1:1 correspondence, the rhythm may be originating in the atria. As such, under certain conditions, SVT discriminator 114 is enabled to perform additional analysis of the EGM signal or apply criteria to the EGM signal and/or sense event signals for discriminating SVT from VT or VF. In one embodiment, SVT discriminator 114 performs a morphology analysis, such as wavelet analysis, that involves comparing a sensed R-wave morphology to a normal sinus rhythm R-wave template. If the fast ventricular rate is being conducted from the atria, the R-wave morphology will approximately match a normal sinus rhythm R-wave template.

Examples of wavelet morphology analysis techniques useful for implementation in SVT discriminator module 114 are generally described in commonly-assigned U.S. Pat. No. 6,393,316 (Gillberg, et al.) and U.S. Pat. No. 7,242,978 (Cao, et al), both of which patents are hereby incorporated herein by reference in their entirety. Other morphology analysis techniques or other techniques that do not necessarily rely on a morphology comparison may be used for performing SVT discrimination. Other techniques for identifying a supraventricular rhythm may be implemented in SVT discriminator module 114.

Sensing analyzer 116 is configured to detect likely occurrences of undersensing and/or oversensing. In one embodiment, sensing analyzer 116 is configured to detect T-wave oversensing. Methods for detecting T-wave oversensing are generally disclosed in U.S. Pat. No. 7,783,354 (Gunderson) and U.S. Pat. No. 7,831,304 (Cao, et al.), both of which patents are hereby incorporated herein by reference in their entirety. However, the techniques disclosed herein are not limited to a particular method for detecting T-wave oversensing and any technique that reliably detects likely occurrences of T-wave oversensing may be used.

When T-wave oversensing is present, the rate-based detection module 112 may detect a cardiac rhythm in the VT or VF zone due to T-waves being sensed as R-waves. As will be described herein, the sensing analyzer 116 is enabled to analyze the EGM signal under certain conditions in order to reduce the occurrence of an improper shock therapy by precluding a false positive VT or VF detection due to oversensing, and, under other conditions, in order to positively detect a true SVT episode when rate-based detection module 112 detects a ventricular rate in the VT or VF therapy zone due in part to T-wave oversensing.

For example, if a VT or VF detection is made, and the ventricular rate is faster than the SVT limit, sensing analyzer may evaluate the ventricular signal for TWOS to prevent a VT or VF therapy from being delivered when TWOS is causing the sensed ventricular rate to fall in a therapy zone. When TWOS is accounted for, the true underlying ventricular rate is not in a therapy zone and therefore therapy is not delivered.

Under a different set of conditions, sensing analyzer 116 is enabled to detect TWOS once a VT or VF detection is made, and if TWOS is detected and contributing to a true ventricular rate that is still in a therapy zone and the ventricular rate is less than the SVT limit, SVT discriminator 114 is enabled to apply SVT discrimination criteria. Under these conditions, the sensing analyzer 116 is enabled to determine if SVT discriminator 114 should be enabled to discriminate between a ventricular rate in the therapy zone being either a true ventricular tachycardia or an SVT.

In some embodiments, sensing analyzer 116 is also configured to evaluate the EGM signal for detecting undersensing. An example of a method for determining the presence of undersensing may be found, for example, in U.S. Pat. No. 8,073,536 to Gunderson et al., incorporated herein by reference in it's entirety. If P-waves are being undersensed, the rate-based detection module 112 may detect a ventricular rate faster than the undersensed atrial rate. If the ventricular rate meets rate-based VT or VF detection criteria, sensing analyzer 116 may be invoked during the detection algorithm to evaluate the atrial signal for possible undersensing. If undersensing is detected, SVT discriminator 114 is enabled to properly discriminate between VT/VF and SVT when the ventricular rate is in a therapy zone.

Control unit 106 responds to a cardiac rhythm episode classification from rhythm detection module 110 by controlling therapy delivery module 104 to either deliver or withhold a therapy as appropriate. When rhythm detection module 110 detects an SVT episode, a shock therapy is withheld. If a VT or VF episode is detected, therapy delivery module 104 is controlled to deliver therapy according to a menu of programmed therapies. If a VT or VF episode is detected based on rate/interval analysis but is not confirmed due to detecting TWOS (true ventricular rate not in a therapy zone), therapy is withheld.

Telemetry module 118 is used for transmitting data accumulated by IMD 10 wirelessly to external device 30. Examples of communication techniques used by IMD 10 include low frequency or radiofrequency (RF) telemetry, which may be an RF link established via Bluetooth, WiFi, or MICS. IMD 10 receives programming commands from external device 30 via telemetry 118.

Figure 3:
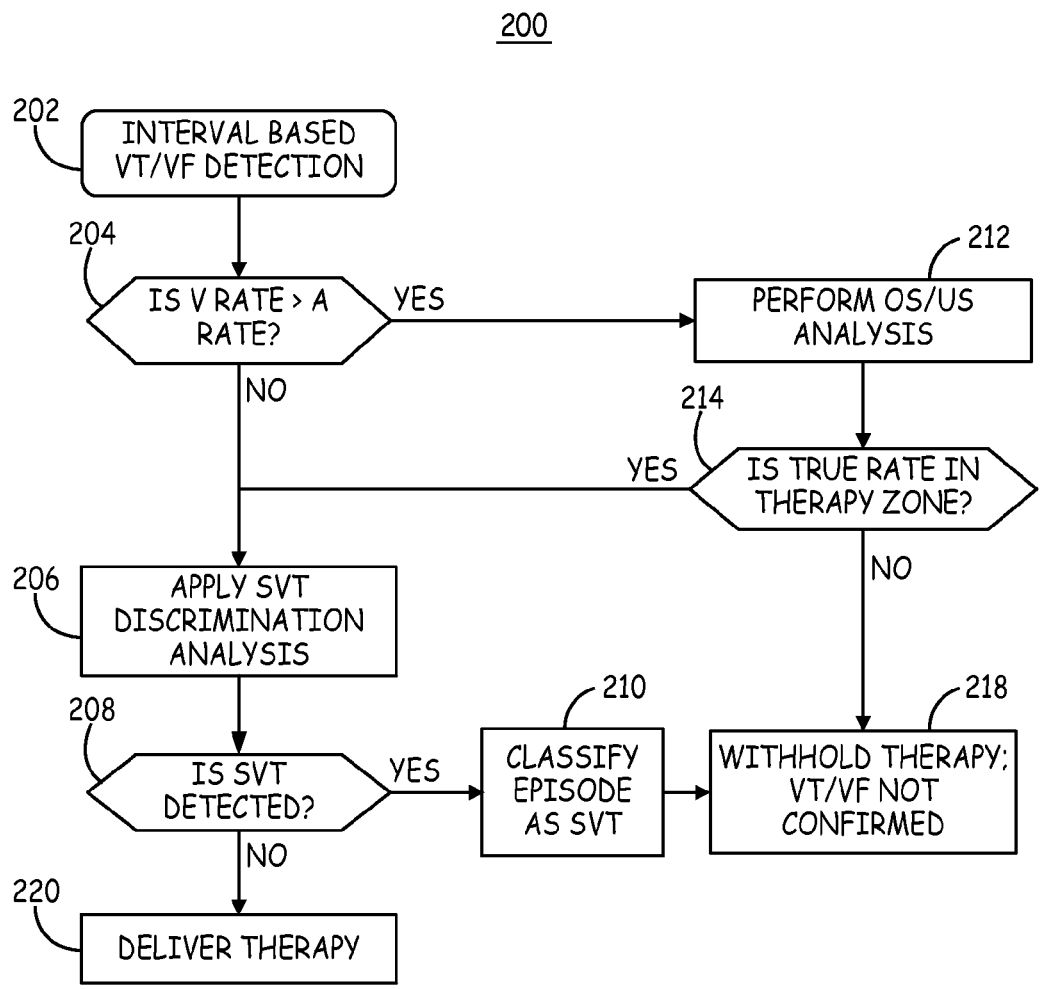
FIG. 3 is a flow chart of a method for discriminating cardiac rhythm episodes according to one embodiment.

FIG. 3 is a flow chart 200 of a method for discriminating cardiac rhythm episodes according to one embodiment. Flow chart 200 and other flow charts presented herein are intended to illustrate the functional operation of the medical device system, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 202, an interval or rate-based detection of VT or VF is made by rate-based detection module 110. If the sensed ventricular rate is not faster than the sensed atrial rate (no branch of decision block 204), the SVT discriminator 114 is enabled to apply discrimination criteria at block 206. If SVT is not detected ("no" branch of block 208), a therapy is delivered to treat the confirmed VT or VF at block 220. If SVT is detected based on the discrimination analysis ("yes" branch of block 208), the detected episode is classified as SVT (block 210), and therapy is withheld (block 218)

The condition of the sensed ventricular rate being greater than the atrial rate ("yes" branch of block 204), may indicate a true VT or VF but may be due to the presence of T-wave oversensing or atrial undersensing. As such, in response to a rate-based VT or VF detection when the ventricular rate is greater than the atrial rate ("yes" branch of block 204), the sensing analyzer 116 is enabled to analyze the EGM signal for oversensing (OS) and/or undersensing (US) at block 212.

TWOS may be detected if a threshold number of T-wave analysis windows indicate T-wave oversensing. For example, if at least 6 out of 20 T-wave analysis windows occur contemporaneously with VT or VF intervals, TWOS is detected. If T-wave oversensing is detected, the T-wave oversensing is accounted for at block 214 to determine if a "true" underlying ventricular rate is still in a therapy zone. This determination may be made according to a number of techniques. For example, each oversensed T-wave may be removed and RR intervals may be recalculated to determine if interval-based detection criteria are still met.

When the "true" rate is still in the therapy zone after accounting for oversensing intervals ("yes" branch of block 214), the SVT discriminator is enabled to perform SVT discrimination analysis at block 206. In this way, if a sensed ventricular rate is greater than the atrial rate and T-wave oversensing is present, SVT discrimination is enabled to allow the IMD 10 to discriminate and positively classify a cardiac episode as SVT per the outcome of the SVT discrimination analysis.

If the "true" ventricular rate is no longer in the therapy zone after accounting for detected TWOS ("no" branch of block 214), therapy is withheld and the VT or VF episode is not confirmed (block 218). A positive detection of an SVT episode is not made, but the VT or VF episode is unconfirmed and no therapy is delivered.

Figure 4:
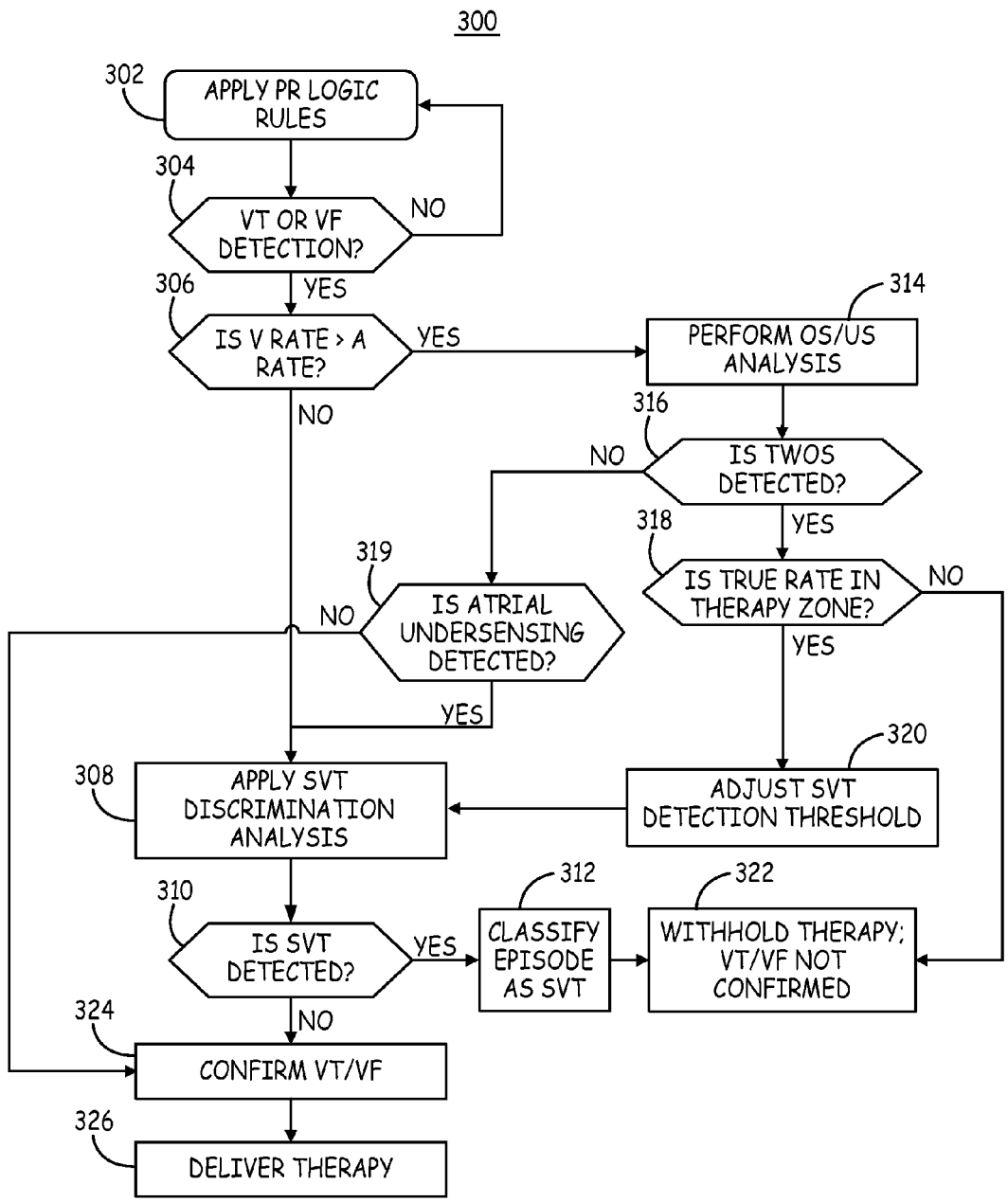
FIG. 4 is a flow chart of a method for discriminating cardiac rhythm episodes according to another embodiment.

FIG. 4 is a flow chart 300 of a method for discriminating cardiac rhythm episodes according to another embodiment. At block 302, rhythm detection module 110 applies PR Logic rules for detecting VT or VF according to rate and interval analysis criteria. The possible outcomes of applying PR Logic may be that an SVT detection is made (not shown), a dual tachycardia detection is made, no detection is made (not shown), or a VT or VF detection is made depending on the types or rules implemented and applied and the underlying rhythm. If a VT or VF detection is made, at decision block 304, the ventricular rate is compared to the atrial rate at block 306. When the ventricular rate is not greater than the atrial rate, the SVT discriminator is enabled to perform SVT discrimination at block 308. As described above, in one embodiment, the SVT discriminator 114 applies a wavelet morphology analysis. The use of PR logic and wavelet morphology discrimination are generally described in U.S. Pat. No. 7,031,771 (Brown et al.), previously incorporated herein.

If the ventricular rate is greater than the atrial rate at block 306, sensing analysis is performed at block 314. If TWOS is detected as determined at block 316, a determination is made if the true ventricular rate is in the therapy zone after accounting for TWOS. If the true underlying ventricular rate, after ignoring or accounting for over-sensed T-waves, is not in a therapy zone, therapy is withheld at block 322. No analysis for SVT is performed and no positive SVT detection is made.

If the ventricular rate is still in the therapy zone, an SVT detection threshold or criterion is adjusted at block 320. The SVT detection threshold or criterion is applied by SVT discriminator 114 in discriminating SVT from VT or VF. The SVT detection threshold or criterion is adjusted at block 320 to be less stringent than a threshold normally applied by SVT discriminator when TWOS has not been detected.

For example, the SVT discriminator may be configured to compare the morphology of a sensed R-wave (during or leading up to detection) to a previously established normal sinus rhythm (NSR) or SVT R-wave template. A morphology matching score may be computed and compared to a match threshold. If the matching score meets or exceeds the match threshold, the R-wave is detected as being conducted from the atria. The criteria for detecting SVT may require that at least three out of eight R-waves analyzed match the NSR or SVT template in order to detect SVT. This threshold of three out of eight R-waves may be reduced to two out of eight R-waves, for example, in response to detecting TWOS. The lower threshold number of matching R-waves is a less stringent criterion for detecting SVT when TWOS has been detected as compared to the threshold used when SVT discrimination analysis block is arrived at from the "no" branch of block 306. This less stringent criterion takes into account that some sensed R-waves may be oversensed T-waves.

After adjusting the SVT detection threshold at block 320, the SVT discriminator 114 is enabled to perform SVT discrimination analysis at block 308. If SVT is detected, an output is produced by rhythm detection module 110 positively classifying the rhythm episode as an SVT at block 312. Accordingly, even though the sensed ventricular rate was greater than the atrial rate at block 306, which would normally be interpreted as strong evidence of VT or VF and might preclude SVT analysis in other detection algorithms, SVT discrimination is enabled if TWOS is detected and the true underlying ventricular rate is still in the therapy zone. If the less stringent SVT detection criterion is met, SVT is positively detected at block 312. Conversely, if SVT is not detected, an output may be produced by rhythm detection module 110 affirming that SVT is not detected, i.e. confirming a VT or VF detection, at block 324.

It is understood that TWOS analysis may be performed at other times during or in parallel to the algorithm shown in FIG. 4. However, in those cases, TWOS is generally performed to prevent a false positive VT or VF detection due to TWOS thereby reducing the likelihood of an inappropriate shock therapy. In the algorithms shown by the flow chart 300 of FIG. 4 and the flow chart 200 of FIG. 3, SVT discrimination is performed after a VT or VF detection is made, a sensed ventricular rate is greater than an atrial rate, and TWOS is detected but a true underlying rate still falls in a therapy zone to allow a positive SVT episode classification to be made if SVT detection criteria are met.

In addition or alternatively to performing a sensing analysis for TWOS, an analysis for atrial undersensing may be performed. Examples of methods for detecting atrial undersensing are generally disclosed in U.S. Pat. No. 6,129,745 (Sun et al.), and U.S. Pat. Application Publication No. 2011/0112417 (Gunderson, et al.), both of which are incorporated herein by reference in their entirety. The techniques described herein are not limited to any particular method for detecting atrial undersensing. Rather, any reliable method for detecting the P-wave undersensing may be used.

For example, according to one embodiment, the determination as to whether undersensing has occurred may be made by determining whether one of a predetermined number of undersensing criteria have been met. An examples of an undersensing criteria would include determining whether at least one sensed AA interval associated with predetermined beats, such as the NID ventricular beats prior to detection of the event and the atrial interval immediately subsequent to the detection of the event for example, greater than a predetermined interval, such as 2500 ms for example. Another example of an undersensing criteria would include determining whether the atrial channel includes less than a predetermined number of events, such as nine events for example, prior to detection.

Another example of an undersensing criteria according to the present disclosure would include calculating a median atrial interval in a sliding window of a predetermined number of intervals, such as eight intervals for example, and determining whether the median atrial interval is greater than a predetermined threshold, such as 1300 ms for example. If the median atrial interval is greater than the predetermined threshold, atrial undersensing is determined to have occurred. Atrial undersensing is also determined to have occurred if the median is greater than a predetermined threshold, such as 350 ms for example and a current atrial interval, such as the final atrial event in the window for example, i.e., the eighth event, is greater than the median by a predetermined threshold, such as 1.7 times the median interval or more, for example. Atrial undersensing is also determined to have occurred if the median is within a predetermined range, such as greater than 200 ms and less than or equal to 359 ms for example, and a current atrial interval, such as the final atrial event in the window for example, i.e., the eighth event, is greater than the median by a predetermined threshold, such as 1.9 times the median interval or more, for example. Atrial undersensing may be determined to have occurred if the median is greater than 0 ms and less than or equal to 200 ms, and a current atrial interval, such as the final atrial event in the window for example, i.e., the eighth event, is greater than the median by a predetermined threshold, such as 3.25 times the median interval or more, for example.

Another criteria for determining whether atrial undersensing has occurred, according to an embodiment of the present disclosure, may include determining whether there are two or less intervals in the entire record that are two times the median AA interval, or three times the median AA interval and a majority of the AA intervals are regular, and there is a depolarization on the atrial egm signal where the expected atrial event would have occurred. For example, regular AA intervals (approximately equal to 300 ms) are sensed for a majority of the sensed atrial events $A_s$, such as 92% for example, and there is only one or two depolarizations that are either an interval 965 that is 900 ms and therefore three times the median AA interval (300 ms), or an interval 967 that is 600 ms and therefore two times the median AA interval, and for each interval 965 and 967 there is an associated depolarization, 969 and 971 respectively, on the atrial EGM.

A final exemplary criteria for determining atrial undersensing has occurred includes determining whether a predetermined number of the AA intervals in the entire record are within a predetermined range of the median of the AA intervals, such as 92% within the range of the median, and there are less than or equal to four long intervals, i.e., two or three times the median interval, when the EGM is not stored.

If atrial undersensing is detected at block 319, the SVT discriminator 114 is enabled at block 308. A sensed ventricular rate greater than a sensed atrial rate (block 306) may be the result of undersensing P-waves. As such, if atrial undersensing is detected, the SVT discrimination analysis is performed at block 308 using the standard detection threshold criteria, i.e. the same criteria applied if SVT discrimination is enabled in response to a VT or VF detection being made and a ventricular rate not being greater than an atrial rate (as shown by "no" branch of block 306). If no undersensing or oversensing is detected ("no" branch of block 319), the rate-based VT or VF detection is confirmed at block 324. Therapy is delivered at block 326 to terminate the ventricular tachyarrhythmia.

The SVT discriminator is configured to operate, therefore, using two different SVT detection thresholds in some embodiments. A first normal threshold is applied when the SVT discriminator is enabled in response to a ventricular rate not be greater than an atrial rate ("no" branch of block 306) and in response to detecting atrial undersensing ("yes" branch of block 319). A second threshold less stringent than the first threshold (i.e. easier to detect SVT) is applied when the SVT discriminator is enabled in response to TWOS detection and the true ventricular rate is still in the therapy zone ("yes" branch of block 318). The less stringent SVT detection threshold makes it easier to detect SVT in the presence of T-wave oversensing.

If SVT is not detected at block 310, the rate-based VT or VF detection is confirmed at block 324. A therapy is delivered according to a programmed menu of therapies at block 326. If SVT is detected (block 310), the episode is positively classified as SVT at block 312. Therapy is not delivered (block 322).

Thus, a system and method for detecting and classifying cardiac rhythm episodes have been presented in the foregoing description with reference to specific embodiments. It is appreciated that various modifications to the referenced embodiments may be made without departing from the scope of the disclosure as set forth in the following claims.

The invention claimed is:

1. A medical device for detecting cardiac tachyarrhythmia episodes and delivering therapy, comprising:
a sensing module to sense cardiac events;
a therapy delivery module; and
a detection module configured to:
determine intervals between the sensed cardiac events;
determine a predetermined cardiac episode is occurring in response to the determined intervals;
determine whether a ventricular rate is greater than an atrial rate in response to the determined intervals;
determine whether undersensing or oversensing is occurring in response to the ventricular rate being greater than the atrial rate;
perform a supraventricular tachycardia (SVT) discrimination analysis;
and control the therapy delivery module to deliver therapy in response to the SVT discrimination analysis;
wherein, if oversensing is determined to be occurring, the detection module is further configured to:
adjust the determined intervals to generate an adjusted ventricular rate;
determine whether the cardiac episode is occurring in response to the adjusted ventricular rate; and perform the supraventricular tachycardia (SVT) discrimination analysis in response to the cardiac episode occurring in response to the adjusted ventricular rate; and wherein the SVT discrimination analysis is performed using a first SVT detection threshold in response to the ventricular rate not being greater than the atrial rate or in response to determining undersensing is occurring, and a second SVT detection threshold in response to determining oversensing is occurring, wherein the second SVT detection threshold is different than the first SVT detection threshold.

2. The medical device of claim 1, wherein the detection module is configured to withhold therapy delivery in response to the cardiac episode not occurring in response to the adjusted ventricular rate.

3. The medical device of claim 1, wherein the cardiac episode comprises a ventricular arrhythmia.

4. The medical device of claim 1, wherein performing the SVT discrimination analysis comprises determining a number of cardiac event signals correlated to a supraventricular morphology, the first SVT detection threshold being a first number of sensed cardiac events correlated to a supraventricular morphology and the second SVT detection threshold being a second number of sensed cardiac events correlated to the supraventricular morphology, the second number being less than the first number.

5. The medical device of claim 1, wherein the detection module is configured to compare sensed cardiac events to an SVT threshold, and adjust the second SVT detection threshold in response to the cardiac episode occurring in response to the adjusted ventricular rate.

6. A method for detecting cardiac tachyarrhythmia episodes and delivering therapy, comprising:
sensing cardiac events;
determining intervals between the sensed cardiac events;
determining a predetermined cardiac episode is occurring in response to the determined intervals;
determining whether a ventricular rate is greater than an atrial rate in response to the determined intervals;
determining whether undersensing or oversensing is occurring in response to the ventricular rate being greater than the atrial rate;
performing a supraventricular tachycardia (SVT) discrimination analysis; and
delivering therapy in response to the SVT discrimination analysis, wherein the method further comprises:
if oversensing is determined to be occurring:
adjusting the determined intervals generate an adjusted ventricular rate;
determining whether the cardiac episode is occurring in response to the adjusted ventricular rate;
performing a supraventricular tachycardia (SVT) discrimination analysis in response to the cardiac episode occurring in response to the adjusted ventricular rate; and
wherein the SVT discrimination analysis is performed using a first SVT detection threshold in response to determining undersensing is occurring or in response to the ventricular rate not being greater than the atrial rate and is performed using a second SVT detection threshold in response to determining oversensing is occurring, wherein the second threshold different than the first threshold.

7. The method of claim 6, further comprising withholding therapy delivery in response to the cardiac episode not occurring in response to the adjusted ventricular rate.

8. The method of claim 6, wherein the cardiac episode comprises a ventricular arrhythmia.

9. The method of claim 6, wherein performing the SVT discrimination analysis comprises determining a number of cardiac event signals correlated to a supraventricular morphology, the first SVT detection threshold being a first number of sensed cardiac events correlated to a supraventricular morphology and the second SVT detection threshold being a second number of sensed cardiac events correlated to the supraventricular morphology, the second number being less than the first number.

10. The method claim 6, further comprising:
comparing sensed cardiac events to an SVT threshold; and
adjusting the second SVT detection threshold in response to the cardiac episode occurring in response to the adjusted ventricular rate.

11. A non-transitory, computer-readable medium comprising instructions for causing a detection module of a medical device to perform a method, the method comprising:
sensing cardiac events;
determining intervals between the sensed cardiac events;
determining a predetermined cardiac episode is occurring in response to the determined intervals;
determining whether a ventricular rate is greater than an atrial rate in response to the determined intervals;
determining whether undersensing or oversensing is occurring in response to the ventricular rate being greater than the atrial rate;
performing a supraventricular tachycardia (SVT) discrimination analysis;
delivering therapy in response to the SVT discrimination analysis, wherein the method further comprises:
if oversensing is determined to be occurring:
adjusting the determined intervals to generate an adjusted ventricular rate;
determining whether the cardiac episode is occurring in response to the adjusted ventricular rate;
performing a supraventricular tachycardia (SVT) discrimination analysis in response to the cardiac episode occurring in response to the adjusted ventricular rate; and
wherein the SVT discrimination analysis is performed using a first SVT detection threshold in response to determining undersensing is occurring or in response to the ventricular rate not being greater than the atrial rate; and is performed using a second SVT detection threshold in response to determining oversensing is occurring, wherein the second threshold different than the first threshold.

12. The computer-readable medium of claim, 11, wherein performing the SVT discrimination analysis comprises determining a number of cardiac event signals correlated to a supraventricular morphology, the first SVT detection threshold being a first number of sensed cardiac events correlated to a supraventricular morphology and the second SVT detection threshold being a second number of sensed cardiac events correlated to the supraventricular morphology, the second number being less than the first number.

* * * * *